(12) United States Patent
Fosaaen

(10) Patent No.: US 9,291,526 B2
(45) Date of Patent: Mar. 22, 2016

(54) OXYGEN SENSING METHOD AND SYSTEM

(71) Applicant: Kerdea Technologies, Inc., Greenville, NC (US)

(72) Inventor: Ken Ervin Fosaaen, Winterville, NC (US)

(73) Assignee: KERDEA TECHNOLOGIES, INC., Greenville, NC (US)

( * ) Notice: Subject to any disclaimer, the term of this patent is extended or adjusted under 35 U.S.C. 154(b) by 272 days.

(21) Appl. No.: 14/073,200

(22) Filed: Nov. 6, 2013

(65) Prior Publication Data

US 2014/0136082 A1    May 15, 2014

Related U.S. Application Data

(60) Provisional application No. 61/725,209, filed on Nov. 12, 2012.

(51) Int. Cl.
*F02D 41/14*    (2006.01)
*G01M 15/10*   (2006.01)
(Continued)

(52) U.S. Cl.
CPC ......... *G01M 15/104* (2013.01); *F02D 41/1445* (2013.01); *F02D 41/1446* (2013.01); *F02D 41/1455* (2013.01); *F02D 41/1458* (2013.01); *F02D 41/2416* (2013.01); *G01N 27/4065* (2013.01); *F01N 2560/025* (2013.01); *F02D 41/2438* (2013.01)

(58) Field of Classification Search
CPC ............. G01M 15/104; F02D 41/1454; F02D 41/1455; F02D 41/1456; F02D 41/2416; F02D 41/1475; F02D 41/1494; F01N 2560/025; G01N 27/4067

USPC .................. 123/443, 672, 697; 701/103, 109; 73/114.69, 114.71, 114.72, 114.73

See application file for complete search history.

(56) References Cited

U.S. PATENT DOCUMENTS

| | | | |
|---|---|---|---|
| 3,915,135 A | 10/1975 | Kushida et al. | |
| 4,245,314 A | 1/1981 | Henrich et al. | |

(Continued)

FOREIGN PATENT DOCUMENTS

| | | |
|---|---|---|
| CN | 101825032 A | 9/2010 |
| EP | 0339585 A2 | 11/1989 |

(Continued)

OTHER PUBLICATIONS

Search Report for ROC (Taiwan) Patent Application No. 102140950 completed Oct. 10, 2015, mailed Oct. 23, 2015.

*Primary Examiner* — Hai Huynh
(74) *Attorney, Agent, or Firm* — Coats & Bennett, PLLC

(57) ABSTRACT

A method of controlling an engine to help achieve a target air:fuel ratio based on data from an oxygen sensor, and related systems. At least one engine operating parameter and a sensed oxygen level are determined at two or more points in one of a rich and lean region based on data from the oxygen sensor. This information is used to help control engine operation in the other of the rich and lean regions without using directly sensed oxygen level data from that region. Thus, a control paradigm is developed in a first operating region based on oxygen level data from the oxygen sensor, and then used for control in a different second operating region without direct sensed oxygen level data in that second operating region. In some embodiments, the control paradigm may be adaptive based on changing conditions.

24 Claims, 7 Drawing Sheets

(51) Int. Cl.
*F02D 41/24* (2006.01)
*G01N 27/406* (2006.01)

(56) References Cited

U.S. PATENT DOCUMENTS

| | | | |
|---|---|---|---|
| 4,263,652 A | 4/1981 | Henrich | |
| 4,276,600 A | 6/1981 | Hartford et al. | |
| 4,462,890 A | 7/1984 | Touda et al. | |
| 4,500,412 A | 2/1985 | Takahashi et al. | |
| 4,535,316 A | 8/1985 | Wertheimer et al. | |
| 4,660,407 A | 4/1987 | Takami | |
| 4,744,344 A | 5/1988 | Morozumi | |
| 5,895,591 A | 4/1999 | Kojima | |
| 6,227,033 B1 | 5/2001 | Kainz | |
| 6,256,981 B1 | 7/2001 | Sullivan et al. | |
| 6,382,198 B1 * | 5/2002 | Smith et al. | F02D 41/14 123/673 |
| 6,746,584 B1 | 6/2004 | Wang et al. | |
| 7,567,866 B2 | 7/2009 | Kokubu | |
| 7,769,534 B1 | 8/2010 | Xu et al. | |
| 7,954,365 B2 | 6/2011 | White et al. | |
| 8,086,392 B2 | 12/2011 | Anilovich et al. | |
| 8,532,912 B2 * | 9/2013 | Kawamura et al. | F02D 41/14 701/109 |
| 9,115,660 B2 * | 8/2015 | Sakurai | F02D 41/02 60/286 |
| 2004/0060550 A1 | 4/2004 | Wu et al. | |
| 2006/0271271 A1 | 11/2006 | Chauvin et al. | |
| 2010/0217505 A1 | 8/2010 | Kawamura et al. | |
| 2010/0217506 A1 | 8/2010 | Mizoguchi et al. | |
| 2011/0138783 A1 | 6/2011 | Sakurai | |
| 2011/0186446 A1 | 8/2011 | Fosaaen | |

FOREIGN PATENT DOCUMENTS

| | | |
|---|---|---|
| JP | 0743342 A | 2/1995 |
| JP | 4171803 B2 | 10/2008 |
| JP | 4607163 B2 | 1/2011 |
| TW | 200817581 A | 4/2008 |
| TW | 201139838 A | 11/2011 |
| WO | 2011093975 A3 | 8/2011 |

* cited by examiner

OXYGEN SENSING METHOD AND SYSTEM

This application claims benefit of U.S. Provisional Application No. 61/725,209, filed 12 Nov. 2012, the disclosure of which is incorporated by reference herein in its entirety.

BACKGROUND

This application is directed to oxygen sensors, methods of using oxygen sensors, and related systems for use with internal combustion engines.

As known by those of skill in the art, the air:fuel ratio in internal combustion engines is typically represented by lambda ($\lambda$), with $\lambda$ defined as is the actual air:fuel ratio divided by the air:fuel ratio at the exact stoichiometric mixture. Thus, in mathematical terms $\lambda = \text{air:fuel}_{actual}/\text{air:fuel}_{stoichiometric}$. Values less than 1.0 are fuel-rich (rich), values greater than 1.0 are fuel-lean (lean). For many internal combustion engines, maximum power is achieved around $\lambda = 0.86$, and maximum fuel economy is achieved around $\lambda = 1.45$-$1.55$. As can be appreciated, engine management systems typically focus heavily on controlling $\lambda$. As such, most large internal combustion engines have oxygen sensors to sense exhaust gas oxygen levels, with the data from the oxygen sensor used by the engine management systems for various engine management functions. For smaller internal combustion engines, such as those used in motorcycles, all-terrain vehicles, recreational marine applications, and unmanned air vehicles, the size constraints of the engines presents difficulties in identifying suitable oxygen sensors.

Fortunately, small resistive-based oxygen sensors are known, see, for example, U.S. Patent Application Publication 2011/0186446. Such oxygen sensors find a particular application in engine management control for small internal combustion engines. In addition, such sensors are useful for individual cylinder control in multi-cylinder engines and hybrid engines for automotive and off-road applications.

The 2011/0186446 oxygen sensor may be considered as a switching oxygen sensor with some unique properties. Such sensors have a drastic change (orders of magnitude) in the resistance of the sensor element when transitioning across the stoichiometric boundary in air:fuel ratio of Lambda ($\lambda$)=1.00. For example, for the n-type semiconductor version of the 2011/0186446 sensor, above this crossover point (in the lean region with $\lambda > 1.00$), the sensor's resistance is very high and not significantly responsive to changes in the oxygen content in the gasses to which it is exposed; however, below this crossover point (in the rich region with $\lambda < 1.00$) the resistance is significantly lower and has a positive relationship with oxygen content. Conversely, for the p-type semiconductor version of the 2011/0186446 sensor, the resistance is very high in the rich region, but is lower and has a positive relationship with oxygen content in the lean region. Because the sensor has a measurable relationship over part of the overall lambda range, the different versions of the 2011/0186446 sensor may be thought of as a "semi-wideband oxygen sensor."

While the 2011/0186446 sensor is useful for many situations, such as those described in the 2011/0186446 publication, there remains a need for alternative oxygen sensor arrangements, and for alternative methods of oxygen sensing and controlling engines based on the sensed oxygen level(s), and related systems.

SUMMARY

In general, the present invention is directed to a method of controlling an engine to achieve a target air:fuel ratio based on data from an oxygen sensor, and related systems.

In one or more embodiments, at least one engine operating parameter (e.g., fuel metering rate) and a sensed oxygen level are determined at two or more points in one of a rich and lean region based on data from the oxygen sensor. This information is used to help control engine operation in the other of the rich and lean regions without using oxygen level data from that region. Thus, a control paradigm is developed in a first operating region based on oxygen level data from the oxygen sensor, and then used for control in the opposing second operating region without direct sensed oxygen level data in that second operating region. In some embodiments, the control may be adaptive based on changing conditions.

In an illustrative embodiment, a method of controlling an internal combustion engine is provided. The engine is capable of operating both in a rich mode where an air:fuel ratio supplied to a combustion chamber of the engine is below stoichiometric, and in a lean mode where the air:fuel ratio supplied to the combustion chamber is above stoichiometric. The method includes both a) determining both a first parameter value of a first engine parameter and a first sensed value of an oxygen sensor disposed in an exhaust plenum of the internal combustion engine while the engine is operating at a first air:fuel ratio point in the rich mode; and b) thereafter, determining both a second parameter value of the first engine parameter and a second sensed value of the oxygen sensor while the engine is operating at a second air:fuel ratio point in the rich mode, the second point being different from the first point. The method includes thereafter, switching the operation of the engine to the lean mode and controlling operation of the engine in the lean mode based on the first sensed value, the second sensed value, the first parameter value, and the second parameter value. The controlling the operation of the engine in the lean mode may comprise estimating a target parameter value of the first engine parameter to achieve a target air:fuel ratio based on the first sensed value, the second sensed value, the first parameter value, and the second parameter value; and controlling the engine so that the first engine parameter assumes the target parameter value. The method may further include, for greater accuracy, prior to switching operation of the engine to the lean mode, determining both a third parameter value of the first engine parameter and a third sensed value of the oxygen sensor while the engine is operating at a third air:fuel point in the rich mode, the third point being different from both the first and second points. Thus, the controlling operation of the engine in the lean mode may comprise controlling operation of the engine in the lean mode further based on the third parameter value and the third sensed value.

In some embodiments, determining the first sensed value comprises sensing both a resistance and a temperature associated with the oxygen sensor while the engine is operating at the first air:fuel ratio point. In some embodiments, determining the second sensed value comprises sensing both a resistance and a temperature associated with the oxygen sensor while the engine is operating at the second air:fuel ratio point. In some embodiments, the first parameter value is an element of a first set of parameter values corresponding to a plurality of engine parameters; the second parameter value is an element of a second set of parameter values corresponding to the plurality of engine parameters; the target parameter value is an element of a target set of parameter values corresponding to the plurality of engine parameters, and the controlling operation of the engine in the lean mode comprises controlling operation of the engine in the lean mode so that the plurality of engine parameter values assume their corresponding values in the target set of parameter values.

In some embodiments, the controlling may be adaptive (e.g., dynamic). Thus the method may include in response to sensing at least one of a change in ambient environmental conditions and a change in engine operating conditions and a change in engine load, thereafter returning the engine to the rich mode. These embodiments may continue with, while operating the engine in the rich mode: a) determining both a fifth parameter value of the first engine parameter and a fifth sensed value of the oxygen sensor while the engine is operating at a fifth air:fuel ratio point in the rich mode; and b) determining both a sixth parameter value of the first engine parameter and a sixth sensed value of the oxygen sensor while the engine is operating at a sixth air:fuel ratio point in the rich mode, the sixth point being different from the fifth point. These embodiments may continue with thereafter, returning the engine to the lean mode, and controlling operation of the engine while returned to the lean mode based on the fifth sensed value, the sixth sensed value, the fifth parameter value, and the sixth parameter value.

In one or more embodiments, an engine control system for an internal combustion engine is provided. The engine is capable of operating both in a rich mode where an air:fuel ratio supplied to a combustion chamber of the engine is below stoichiometric, and in a lean mode where the air:fuel ratio supplied to the combustion chamber is above stoichiometric. The engine control system comprises a first oxygen sensor disposed in an exhaust plenum of the engine; a second engine parameter sensor configured to sense an engine parameter; a controller comprising one or more processing circuits. The controller is operative to control operations of the engine and configured to: determine both a first parameter value of a first engine parameter and a first sensed value of the oxygen sensor while the engine is operating at a first air:fuel ratio point in the rich mode; thereafter, determine both a second parameter value of the first engine parameter and a second sensed value of the oxygen sensor while the engine is operating at a second air:fuel ratio point in the rich mode, the second point being different from the first point; thereafter, cause the engine switch to operating in the lean mode and control operation of the engine in the lean mode based on the first sensed value, the second sensed value, the first parameter value, and the second parameter value. The engine control system may operate, in various embodiments, according to the various methods described above.

In one or more embodiments, the method is like that described above, but with the lean and rich regions swapped. Thus, the method may include both a) determining both a first parameter value of a first engine parameter and a first sensed value of an oxygen sensor disposed in an exhaust plenum of the internal combustion engine while the engine is operating at a first air:fuel ratio point in the lean mode; and b) thereafter, determining both a second parameter value of the first engine parameter and a second sensed value of the oxygen sensor while the engine is operating at a second air:fuel ratio point in the lean mode, the second point being different from the first point. The method includes thereafter, switching the operation of the engine to the rich mode and controlling operation of the engine in the rich mode based on the first sensed value, the second sensed value, the first parameter value, and the second parameter value. The controlling the operation of the engine in the rich mode may comprise estimating a target parameter value of the first engine parameter to achieve a target air:fuel ratio based on the first sensed value, the second sensed value, the first parameter value, and the second parameter value; and controlling the engine so that the first engine parameter assumes the target parameter value. The method may further include, for greater accuracy, prior to switching operation of the engine to the rich mode, determining both a third parameter value of the first engine parameter and a third sensed value of the oxygen sensor while the engine is operating at a third air:fuel point in the lean mode, the third point being different from both the first and second points. Thus, the controlling operation of the engine in the rich mode may comprise controlling operation of the engine in the rich mode further based on the third parameter value and the third sensed value.

In some embodiments, determining the first sensed value comprises sensing both a resistance and a temperature associated with the oxygen sensor while the engine is operating at the first air:fuel ratio point. In some embodiments, determining the second sensed value comprises sensing both a resistance and a temperature associated with the oxygen sensor while the engine is operating at the second air:fuel ratio point. In some embodiments, the first parameter value is an element of a first set of parameter values corresponding to a plurality of engine parameters; the second parameter value is an element of a second set of parameter values corresponding to the plurality of engine parameters; the target parameter value is an element of a target set of parameter values corresponding to the plurality of engine parameters, and the controlling operation of the engine in the rich mode comprises controlling operation of the engine in the rich mode so that the plurality of engine parameter values assume their corresponding values in the target set of parameter values.

In some embodiments, the controlling may be adaptive (e.g., dynamic). Thus the method may include in response to sensing at least one of a change in ambient environmental conditions and a change in engine operating conditions and a change in engine load, thereafter returning the engine to the lean mode. These embodiments may continue with, while operating the engine in the lean mode: a) determining both a fifth parameter value of the first engine parameter and a fifth sensed value of the oxygen sensor while the engine is operating at a fifth air:fuel ratio point in the lean mode; and b) determining both a sixth parameter value of the first engine parameter and a sixth sensed value of the oxygen sensor while the engine is operating at a sixth air:fuel ratio point in the lean mode, the sixth point being different from the fifth point. These embodiments may continue with thereafter, returning the engine to the rich mode, and controlling operation of the engine while returned to the rich mode based on the fifth sensed value, the sixth sensed value, the fifth parameter value, and the sixth parameter value.

In one or more embodiments, another engine control system for an internal combustion engine is provided. The engine is capable of operating both in a lean mode where an air:fuel ratio supplied to a combustion chamber of the engine is below stoichiometric, and in a rich mode where the air:fuel ratio supplied to the combustion chamber is above stoichiometric. The engine control system comprises a first oxygen sensor disposed in an exhaust plenum of the engine; a second engine parameter sensor configured to sense an engine parameter; a controller comprising one or more processing circuits. The controller is operative to control operations of the engine and configured to: determine both a first parameter value of a first engine parameter and a first sensed value of the oxygen sensor while the engine is operating at a first air:fuel ratio point in the lean mode; thereafter, determine both a second parameter value of the first engine parameter and a second sensed value of the oxygen sensor while the engine is operating at a second air:fuel ratio point in the lean mode, the second point being different from the first point; thereafter, cause the engine switch to operating in the rich mode and control operation of the engine in the rich mode based on the first sensed value, the second sensed value, the first parameter value, and the second parameter value. The engine control system may operate, in various embodiments, according to the various methods described above.

The various aspects discussed above may be used alone or in any combination. The various apparatus disclosed herein may operate according to any combination of various method disclosed herein, and vice versa. Further, the present invention is not limited to the above features and advantages. Indeed, those skilled in the art will recognize additional features and advantages upon reading the following detailed description, and upon viewing the accompanying drawings.

DETAILED DESCRIPTION

In one or more embodiments, the present application is directed to a method of controlling an engine to achieve a target air:fuel ratio based on data from an oxygen sensor, and related systems. At least one engine operating parameter and a sensed oxygen level are determined at two or more points in one of a rich and lean region based on data from the oxygen sensor. This information is used to help control engine operation in the other of the rich and lean regions without using oxygen level data from that region. Thus, a control paradigm is developed in a first operating region based on oxygen level data from the oxygen sensor, and then used for control in the opposing second operating region without direct sensed oxygen level data in that second operating region. In some embodiments, the control may be adaptive based on changing conditions.

For simplicity, the discussion below may generally be in the context of an oxygen sensor for a small displacement gasoline powered internal combustion engine, but it should be understood that the oxygen sensor(s) disclosed herein may be used in other internal combustion engine applications, such a hydrogen powered engines, other hydrocarbon powered engines, diesel engines, Homogeneous Charge Compression Ignition (HCCI) engines, and Reactivity Controlled Compression Ignition (RCCI) engines.

Figure 1:
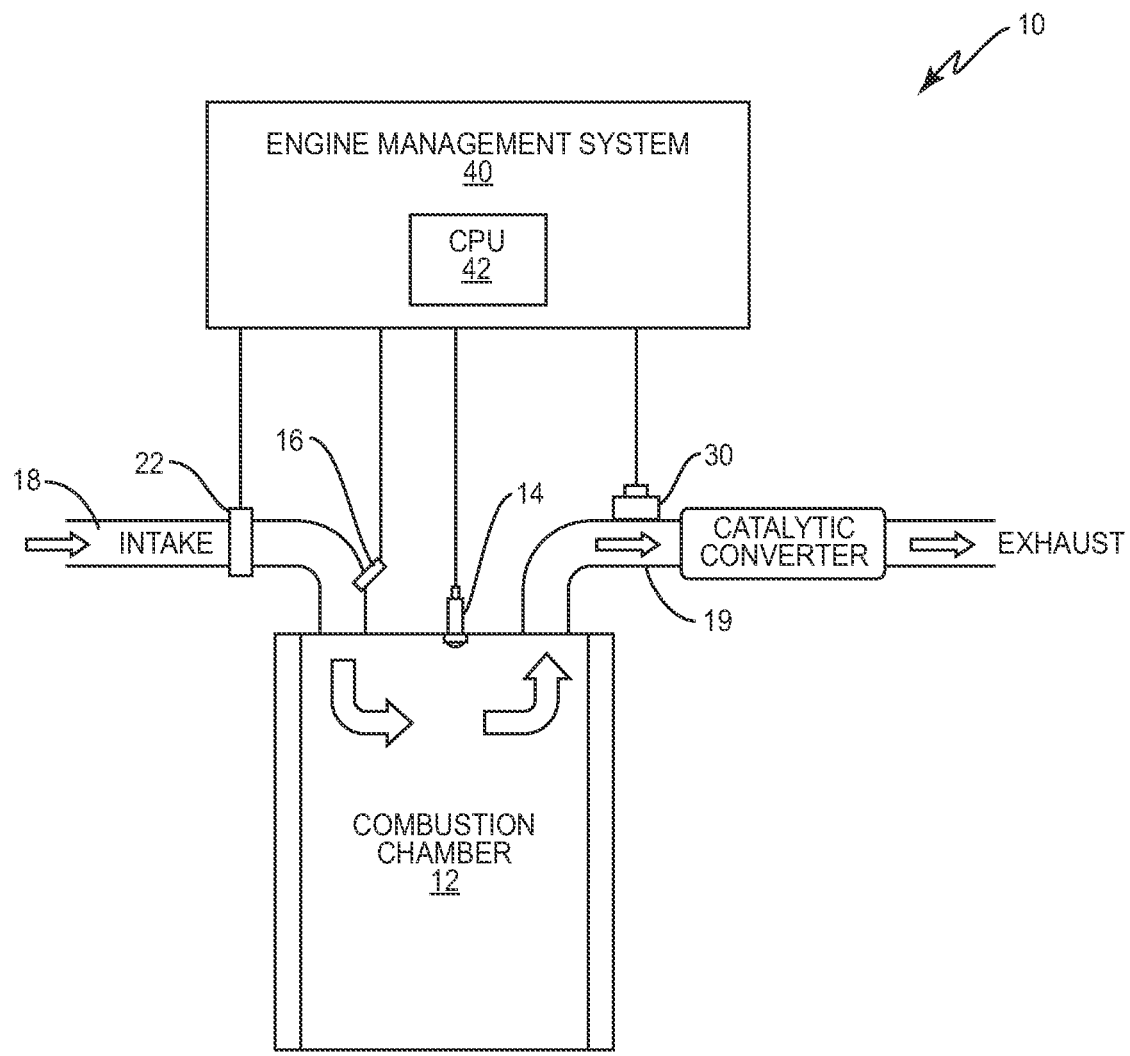
FIG. 1 shows schematic representation of an engine, using the engine controller of one embodiment of the present invention.

FIG. 1 shows a schematic of an internal combustion engine 10, which may be of any type (e.g., piston, rotary, nutating disk, etc.). The engine 10 includes at least one combustion chamber 12 with associated piston, valves, etc. (note shown), an intake manifold 18, an exhaust manifold 19, and an engine management system 40. The intake manifold 18 supplies air to the combustion chamber 12. An mass airflow sensor 22 advantageously with associated temperature sensor is disposed in the intake 18 manifold so that the incoming air conditions may be monitored and/or controlled. A controllable fuel metering system such as a throttle body and fuel injector 16 supplies fuel to the combustion chamber under control of the engine management system 40. For spark ignition engines, a spark ignition device 14, e.g., spark plug, operates under the control of the engine management system 40 to ignite the air and fuel mixture in the combustion chamber 12 at the desired time in the cycle for proper combustion. An oxygen sensor 30 is disposed in the exhaust plenum 19 to sense the amount of oxygen in the exhaust gases, so that the proper air:fuel ratio may be properly metered and maintained. The engine management system 40 includes one or more processing circuits 42 (collectively "controller") that control the fuel supply, ignition timing, and other engine parameters based on the input from the various sensors and the programming of the processing circuits 42. Other than the particulars of the oxygen sensor 30 and the operation of the processing circuit(s) 42 described in greater detail below, the configuration and operations of the engine 10 are well known to those of skill in the art, and are not discussed further herein in the interests of clarity.

Figure 2:
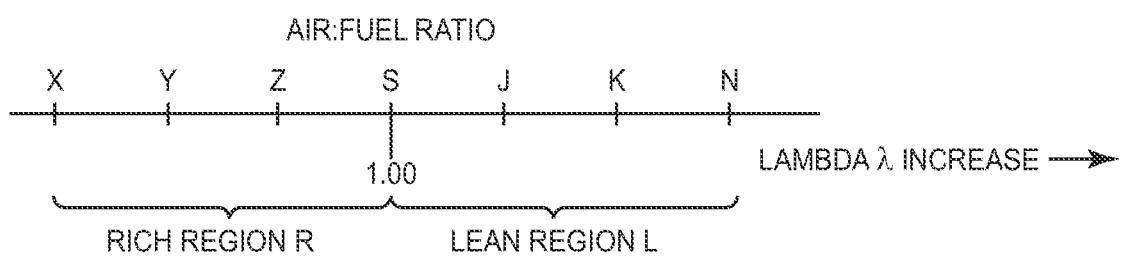
FIG. 2 shows a representation of various air:fuel operating regions for the engine.

As can be appreciated, the engine 10 is able to operate in a rich mode or region R where $\lambda < 1.00$, in a lean mode or region L where $\lambda < 1.00$, and at a stoichiometric point S where $\lambda = 1.00$. Referring to FIG. 2, the engine 10 is able to operate at multiple air:fuel ratio points in the rich region R, such as at points X, Y, and Z. The points X, Y, and Z, may, for example, correspond to $\lambda$ values of 0.85, 0.90, 0.95, respectively. Likewise, the engine 10 is able to operate at a stoichiometric air:fuel point S, and at multiple air:fuel ratio points in the lean region L, such as J, K, and N. The points J, K, and N may, for example correspond to $\lambda$ values of 1.05, 1.10, and 1.20 respectively. The engine management system 40 uses the oxygen sensor 30, as described below, to help control the engine 10 so that the engine 10 operates at the desired air:fuel ratio.

The oxygen sensor 30 is advantageously a resistive-based oxygen sensor, such as those described in U.S. Patent Application Publication No. 2011/0186446, or similar. The '6446 publication discloses, in one or more embodiments, an oxygen sensor that includes an n-type or p-type semiconductor that connects two intermeshing comb type electrodes for functioning as an oxygen sensing portion 32 and a resistance-based heater portion 34. The comb electrodes include a plurality of comb fingers having lengths and spacing. The length and spacing of the comb fingers, and the particular materials, including the semiconducting and catalytic materials, may be adjusted as desired for the particular operating conditions for the sensor 30. For purposes of the initial discussion below, the sensor 30 will be initially assumed to have an n-type semiconductor such that the resistance is significantly lower and has a positive relationship with oxygen content in the rich region R, while the resistance is relatively high and uncorrelated to the oxygen content in the lean region L.

Figure 3:
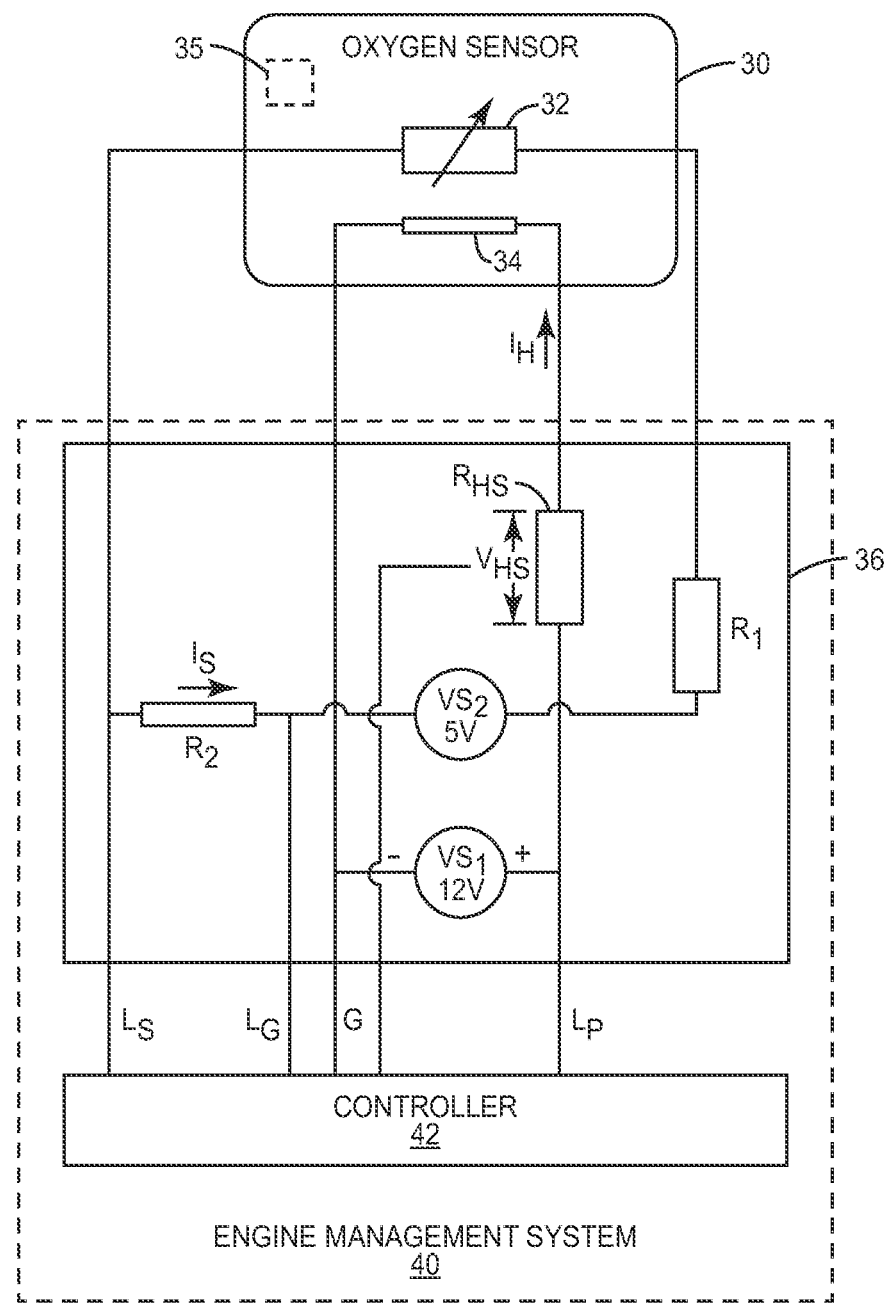
FIG. 3 shows a schematic representation of the oxygen sensor connected to the controller.

Referring to FIG. 3, the oxygen sensor 30 is connected to the controller 42 so that the sensed oxygen level data from the sensor is supplied to the controller 42. In one or more illustrative embodiments, changes in the resistance of the sensor 30 are converted into a voltage signal, such as by being routed through a resistance network 36, so that the controller 42 receives different voltage inputs for different sensed oxygen levels. The resistive network 36 may be as shown in FIG. 3, although such is not required in all embodiments. The resistor network of FIG. 3 includes a shunt resistor $R_{HS}$, resistors $R_1$ and $R_2$, a twelve volt voltage source $VS_A$, a five volt voltage source $VS_2$, a power line $L_P$, a ground line G, an oxygen sense line $L_S$, and a reference line $L_G$. The heater portion 34 is disposed between $L_P$ and G, and is supplied with power from twelve volt power source $VS_1$, via shunt resistor $R_{HS}$. A voltage drop $V_{HS}$ is measured across shunt resistor $R_{HS}$. A voltage drop $VR_2$ is measured across resistor $R_2$, between line $L_S$ and line $L_G$. The controller 42 advantageously receives $L_S$, $L_G$, and $V_{HS}$ used to calculate the relevant values as discussed further below. Note further that voltage drop $V_{HS}$ may be sensed via two leads, one on each side of shunt resistor $R_{HS}$, with each lead feeding a line to controller 42; this arrangement is shown in simplified fashion in FIG. 3 for clarity. Note that the resistance network 36 may be integrated into an oxygen sensor assembly, integrated into the controller 42, be a separate component or components between the oxygen sensor 30 and the controller 42, or dispersed in any suitable manner.

The resistance $R_S$ of the oxygen sensing portion 32 may be determined by any suitable way. For example, the current $I_S$ through the oxygen sensing portion 32 may be calculated as the voltage drop $VR_2$ across resistor $R_2$. Further, the overall resistance $R_{SC}$ along the five volt circuit through resistor $R_1$, oxygen sensing portion 32, and resistor $R_2$ may be calculated as $R_{SC}$=voltage of the circuit divided by current of the circuit, or 5 (volts) divided by $I_S$. Then, the resistance $R_S$ of the oxygen sensing portion 32 may be calculated as $R_S=R_{SC}-R_1-R_2$. Thus, the resistance $R_S$ of the oxygen sensing portion 32 may be determined based on knowledge of the voltage of voltage source $VS_2$, the resistance of resistors $R_1$ and $R_2$, the voltage drop $VR_2$ across resistor $R_2$ (voltage difference between line $L_S$ and $L_G$). In alternate embodiments, resistor $R_1$ may be omitted from the circuit, or additional resistors may be added. If resistor $R_1$ is omitted, then the resistance $R_S$ of the oxygen sensing portion 32 may be calculated as $R_S=R_{SC}-R_2$; or, if additional resistors are added, the calculation of $R_S$ advantageously takes their presence into account. The oxygen level in the exhaust gases may then be determined based on the resistance of the oxygen sensing portion 32.

The controller 42 receives the inputs from the oxygen sensor 30 and other sensors, and controls the operation of the ignition timing and related engine functions. Relevant to the present discussion, the controller 42 causes the engine 10 to operate at two or more air:fuel points in the rich region R, and takes oxygen level readings (via the oxygen sensor 30) and one or more engine parameter readings at each point. Examples of suitable engine parameters include air intake mass, air intake temperature, fuel metering rate, ignition timing, engine speed (rpm), engine load, and the like. The controller 42 then causes the engine 10 to switch to be operating in the lean region L, and controls the engine 10 in the lean region based on the reference relationship between the air:fuel ratio and the engine parameter established in the rich region R. Thus, while the particular n-type oxygen sensing portion 32 of the oxygen sensor 30 is not able to accurately measure the oxygen content while the engine 10 is in the lean region L, due to the response of the n-type semiconductor, the engine 10 may still be controlled to achieve a desired air:fuel ratio in the lean region L, without using oxygen level readings from the oxygen sensor 30 in the lean region L.

Figure 4:
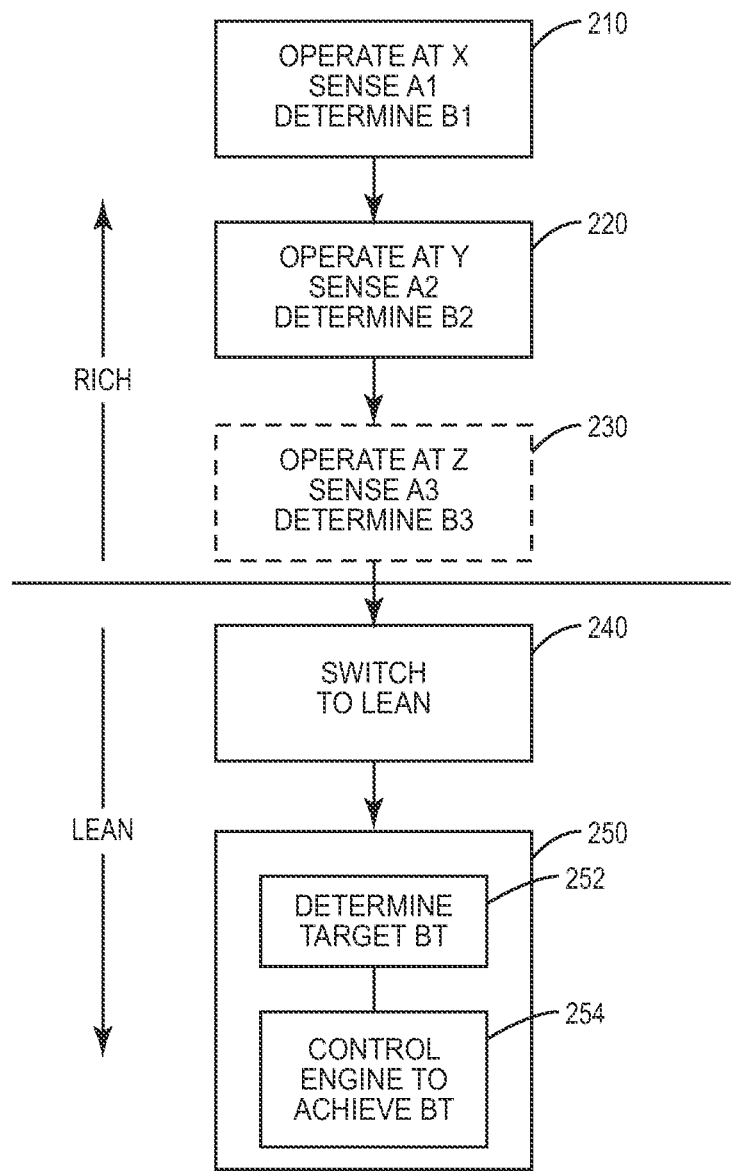
FIG. 4 shows a flowchart of the process of one embodiment of the present invention, where the reference readings are taken in the rich operating region, and the current air:fuel ratio is estimated in the lean operating region.

An exemplary process is shown in FIG. 4. The process begins with the engine 10 operating the rich region R, at a first air:fuel ratio point X (step 210). The oxygen level in the exhaust gas is sensed by the oxygen sensor 30, so that the controller 42 is able to determine a first sensed value A1 of the oxygen sensor 30. The engine parameter B is also sensed, via suitable sensor(s), so that the controller 42 is able to determine a first value B1 of the engine parameter. The controller 42 then causes the engine 10 to operate at another air:fuel point Y in the rich region R (step 220), different from the first point X. A corresponding sensed oxygen value A2 and engine parameter value B2 are then determined for the engine 10 when operating at air:fuel point Y. Based on this data, the controller 42 is able to determine a reference relationship between the sensed oxygen values A and the engine parameter B, for the engine 10 operating in the rich region R.

The controller 42 then causes the engine 10 to switch operation mode, so that the engine 10 operates in the lean region L (step 240). Due to the n-type semiconductor of the oxygen sensing circuit 32 of oxygen sensor 30, there is not a reliable relationship between the resistance of the oxygen sensing circuit 32 and the oxygen level when the engine 10 is operating in the lean region L. However, achieving a desired or target oxygen level, and hence target air:fuel ratio, in the lean region L is useful for the controller 42. As such, the controller 42 controls the engine 10 based on the information gathered while the engine 10 is operating in the rich region R. More particularly, the controller 42 controls the engine in the lean region L based on A1, A2, B1, and B2 (step 250). This controlling may be achieved by determining a target air:fuel ratio TAF, and then determining a target engine parameter value BT by extrapolating the reference relationship between the oxygen level A and the engine parameter B from the rich region R into the lean region L. Thus, the controller 42 may determine a target engine parameter value BT that is estimated to result in the target air:fuel ratio TAF, based on A1, A2, B1, and B2 (step 252). Because the engine parameter is able to be monitored in the lean region L, the controller 42 is able to control the engine so as to achieve the target engine parameter value BT (the current engine parameter value assumes value BT)(step 254), which should result in the target air:fuel ratio TAF being achieved. For example, the controller 42 may control the operation of the engine 10 by causing the fuel supply rate to be increased or decreased.

Note that in the discussion above, two reference air:fuel ratio points in the rich region R were used to establish the reference relationship between A and B. However, the process may advantageously include using three or more reference air:fuel ratio points in the rich region R, in order to better define the relationship. For example, the controller 42, prior to switching the engine 10 operation over to the lean region L (step 240), may cause the engine 10 to operate at a third air:fuel ratio point Z in the rich region R (step 230). A corresponding sensed oxygen value A3 and engine parameter value B3 are then determined for the engine 10 when operating at air:fuel point Z. Then, the controller 42 may control the engine (step 250) in the lean region L based on A1, A2, A3, B1, B2, and B3 (step 250). Thus, the controller 42 may determine the target engine parameter value BT based on the target air:fuel ratio TAF and based on A1, A2, A3, B1, B2, and B3 (step 252). The engine 10 may then be controlled so that the target engine parameter value BT is achieved (step 254). Of course, more than three reference points may alternatively be used using a similar approach.

Similarly, the discussion above has been in the context of one engine parameter B used as the basis for controlling the engine 10. However, instead of a single engine parameter, for example rpm, being used, a set of a plurality of engine parameters, for example rpm, fuel metering rate, exhaust gas temperature, air intake mass, air intake temperature, and the like, may be used. Thus, at point X, values for multiple engine parameters may be determined as a first set, with second, and (optionally) third sets of the same engine parameters determined for points Y, and (optionally) Z. The relevant relationship may then be between A and the set of engine parameters, and a target set of engine parameters determined based on TAF, A1, A2, and optionally A3, and the relevant sets of values (step 252). The engine 10 is then controlled to achieve the engine parameters of the target set (step 254).

The controller 42 uses the process outlined above to establish the relationship between the engine parameter(s) and the value of the sensed oxygen content of the exhaust gas. In some embodiments, the relationship may be established only once, and then used for all future operations. In other embodiments, the controller 42 advantageously adaptively determines the relationship by periodically causing the engine 10 to temporarily return to operate in the rich region R to collect new values for updating the relationship (operate at multiple points, etc.), and then causing the engine to return to operate in the lean region L. In some embodiments, the temporary return to operation in the rich region R to update the relationship may be a triggered response to changing conditions, with the trigger being a detected change in ambient environmental conditions (e.g., incoming air temperature or pressure), and/or a detected change in engine operating conditions (e.g., detection of some fault, detected significant change in exhaust gas temperature, etc.) and/or a detected change in engine load. The reference points used in the updating process may be the same or different, or some same and some different, than used in the original establishment of the reference relationship.

Figure 5:
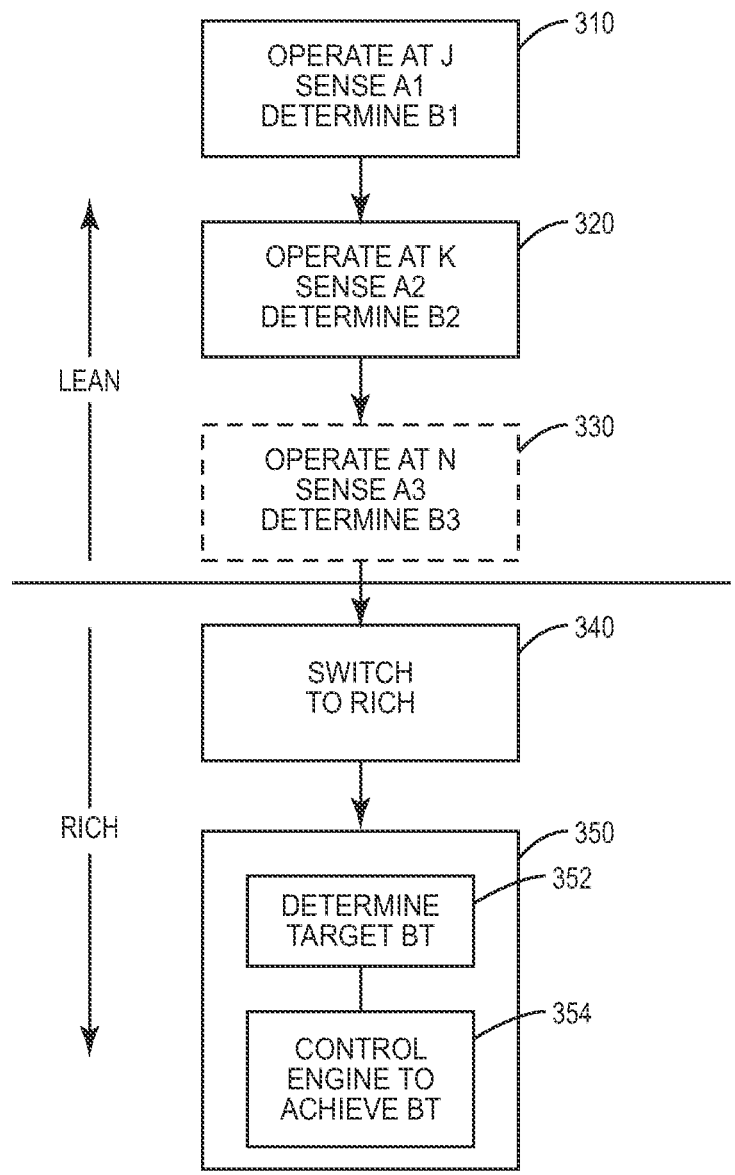
FIG. 5 shows a flowchart of the process of one embodiment of the present invention, where the reference readings are taken in the lean operating region, and the current air:fuel ratio is estimated in the rich operating region.

Note that the discussion above has been in terms of establishing a baseline relationship between A and B (or A and several B's) in the rich region R, and then determining a current air:fuel ratio FC when operating in the lean region L. Such an approach is appropriate for an oxygen sensor 30 using an n-type semiconductor. However, a similar approach may also be used with the roles of the rich and lean regions reversed when the oxygen sensor 30 instead uses a p-type semiconductor. Thus, as shown in FIG. 5, the baseline relationship between A and B (or A and a set of B's) may be determined based on data from operating the engine 10 in the lean region L, and then the engine 10 switched to rich region R, and the engine controlled in the rich region R based on A1, A2, B1, and B2. Thus, the controller 42 may cause the engine 10 to operate at air:fuel ratio point J in the lean region L, collect value A1 corresponding to the sensed oxygen level, and determine the corresponding value B1 of the engine parameter (step 310). The controller 42 may then cause the engine 10 to operate at air:fuel ratio point K in the lean region L, collect value A2 corresponding to the sensed oxygen level, and determine the corresponding value B2 of the engine parameter (step 320). The controller 42 may then optionally cause the engine 10 to operate at air:fuel ratio point N in the lean region L, collect value A3 corresponding to the sensed oxygen level, and determine the corresponding value B3 of the engine parameter (step 330). The controller 42 may then cause the engine 10 to switch operation to the rich region R (step 340). The controller 42 then controls the engine in the rich region R based on A1, A2, B1, B2 (step 350). Thus, the controller 42 may determine a target air:fuel ratio TAF, and then determine BT by extrapolating the reference relationship between the oxygen level A and the engine parameter B from the lean region L into the rich region R (step 352). So, similar to the above, the controller 42 may determine the target engine parameter value BT that is estimated to result in the target air:fuel ratio TAF, based on A1, A2, B1, and B2 (step 352). Because the engine parameter is able to be monitored in the rich region R, the controller 42 is able to control the engine so as to achieve the target engine parameter value BT (the current engine parameter value assumes value BT)(step 354), which should result in the target air:fuel ratio TAF being achieved. Likewise, the multiple engine parameter, updating, and other processes described above with respect to the rich/lean sequence may be similarly followed, with suitable swapping of rich and lean regions/points.

As can be appreciated, various parameters may be considered/measured when establishing the baseline relationship and when estimating the current air:fuel ratio FC. These parameters include, for example, incoming air temperature, incoming air pressure, incoming moisture content, temperature of the oxygen sensor 30 and the like. For example, the temperature of the oxygen sensor 30 may be measured by measuring a resistance associated with the heater portion 34 of the oxygen sensor 30 or by a suitable dedicated temperature sensor 35 (the presence of heater portion 34 being optional for some embodiments). For example, the current $I_H$ in the heater portion 34 may be calculated as the voltage drop $V_{HS}$ across the shunt resistor $R_{HS}$, divided by the resistance of the shunt resistor $R_{HS}$, or $I_H = V_{HS}/R_{HS}$. Then, the resistance $R_H$ of the heater portion 34 may be calculated based on the voltage drop across the heater portion 34 divided by the current $I_H$ through the heater portion 34. Thus, $R_H$ may be calculated as $R_H = (12 - V_{HS})/I_H$. Note that if $R_H$ is significantly small relative $R_H$, then $R_H$ may be calculated as simply $R_H = 12/I_H$. Then, using $R_H$, temperature T may be calculated using a suitable formula, for example $T = (M \times R_H) + B$, where the slope M and the constant B are dependent on the heater design. As can be appreciated, M and B can be determined in a calibration process, and the relevant values stored in memory of the engine management system 40 for use by the controller 42. This temperature may then be used to help determine the value of the oxygen content based on the resistance of the oxygen sensing portion 32 of the oxygen sensor 30 and the temperature of the oxygen sensor 30. The relevant values, whether based on temperature or not, may be stored in suitable memory (not shown) that is part of or accessible by the controller 42. For example, the memory may contain a lookup table of oxygen sensing portion 32 resistance, heater portion 34 resistance, and air:fuel ratio (expressed as lambda or otherwise), or a series of such lookup tables, indexed for example based on incoming air temperature or pressure. Alternatively, the controller 42 may be programmed with a suitable non-lookup table temperature compensation routine for temperature adjusting the values of oxygen content based on the signal(s) from the oxygen sensing portion 32 and the sensed temperature of the oxygen sensor 30.

Figure 6:
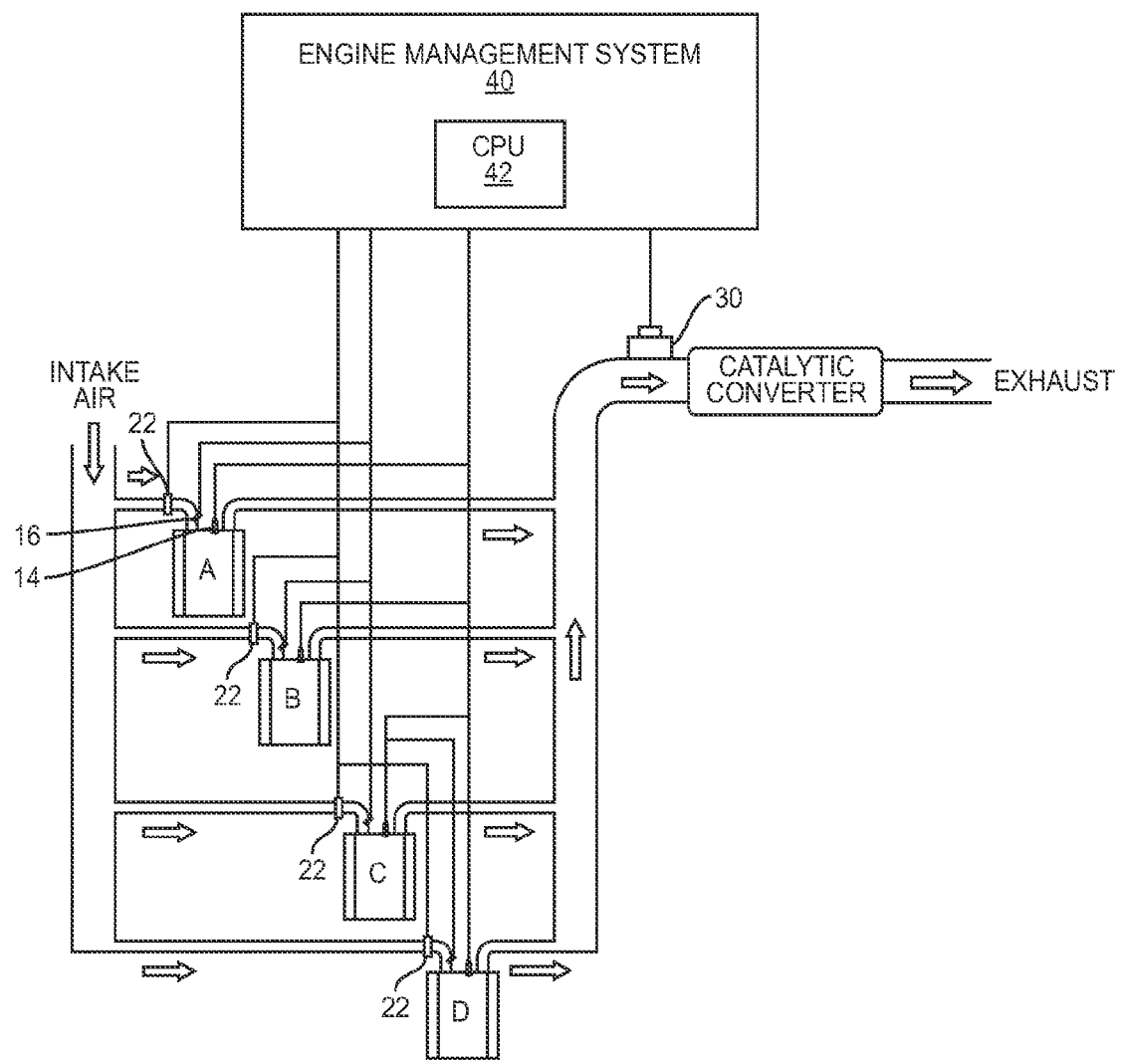
FIG. 6 shows one multiple-cylinder configuration with a common oxygen sensor for all cylinders.
Figure 7:
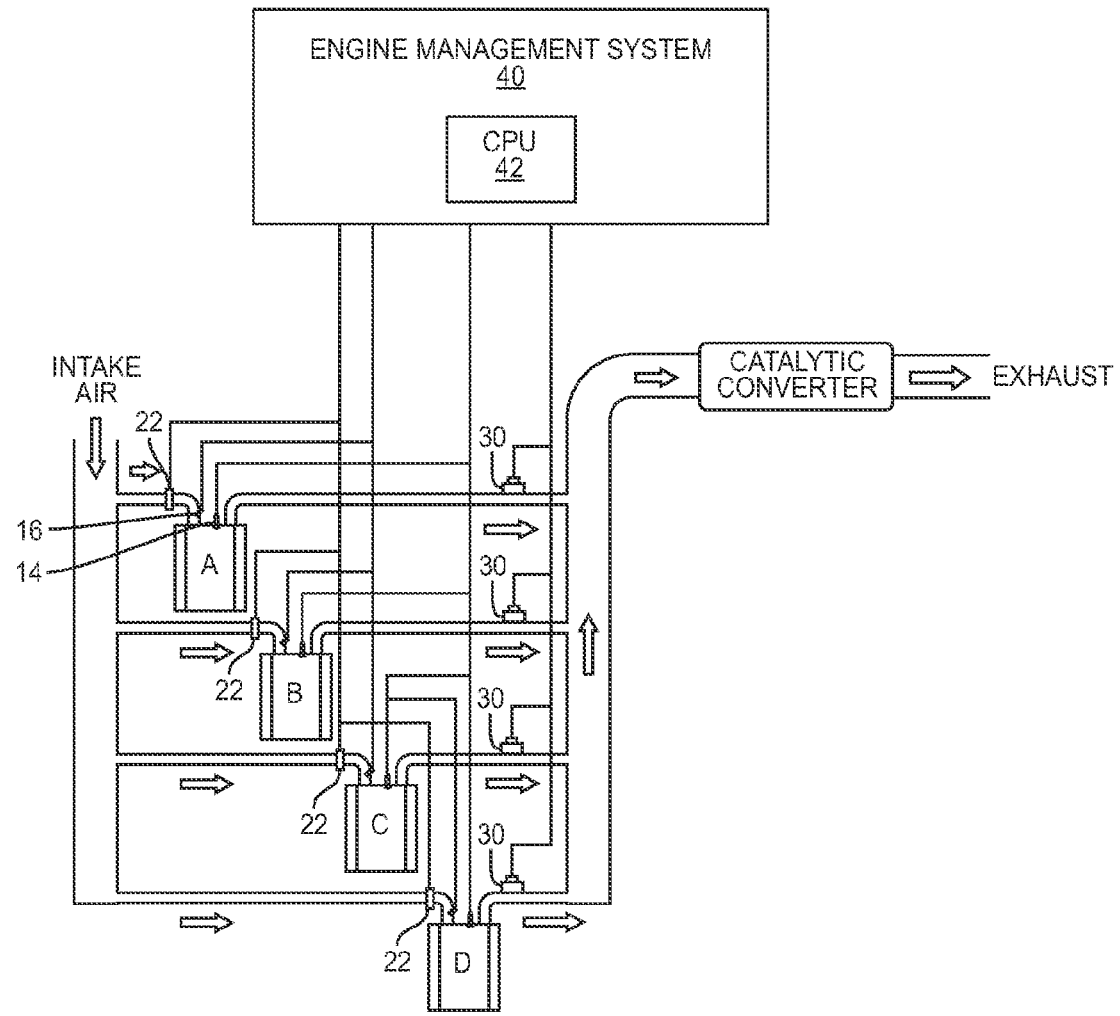
FIG. 7 shows another multiple-cylinder configuration with individual oxygen sensors for each cylinder.

The discussion above has generally been in the context of controlling an engine 10 having a single cylinder/combustion chamber. However, a similar approach may be used with engines having multiple cylinders, such as that shown in FIG. 6 with cylinders A, B, C, and D. In FIG. 6, a single common oxygen sensor 30 is used for multiple cylinders. The controller 42 may control the engine parameters (e.g., fuel metering rate) based on readings from the oxygen sensor 30, or, if the oxygen sensor 30 has fast enough response time, the controller 42 may be able to control the engine parameters on an individual cylinder basis. Another multi-cylinder arrangement is shown in FIG. 7, where each cylinder has its own dedicated oxygen sensor 30. With this arrangement, the controller 42 may more easily control the cylinder-specific engine parameters (e.g., fuel metering rate) on an individual cylinder basis based on readings from the corresponding oxygen sensor 30.

Note that when the engine is operating in the region where the oxygen sensor 30 is able to accurately sense the oxygen level, the controller 42 may control the engine 10 in a conventional close-loop fashion based on the oxygen level data from the oxygen sensor 30.

Note that as used herein, the use of the labels "first", "second", "third", and the like in relation to the various sensed values of the oxygen sensor 30 and the various determined values of the engine parameter(s), and sets thereof, are merely for convenience so as to differentiate between the values, and are not intended to convey a particular sequence or presence. Thus, the relevant values of the oxygen sensor 30 may be the first, second, and fourth values, and there may or may not be a corresponding "third" value and/or the second one may be taken before the first one. Likewise for the engine parameters and sets thereof.

Further, note that as used herein, the term "engine parameter" excludes exhaust oxygen content. As such, sensing or determining an "engine parameter" is different from sensing or determining exhaust gas oxygen content. And, as used herein, an air:fuel ratio may be expressed as an un-normalized ratio (e.g., 14.7:1 for gasoline), or as a normalized ratio (e.g., λ).

The methods and engine control systems discussed above provide the opportunity for enhanced engine control so that greater fuel economy and/or reduced emissions may be achieved.

The disclosure of all patents and patent publications mentioned above are incorporated herein by reference in their entirety.

The present invention may, of course, be carried out in other specific ways than those herein set forth without departing from the scope of the invention. The present embodiments are, therefore, to be considered as illustrative and not restrictive.

What is claimed is:

1. A method of controlling an internal combustion engine, the engine capable of operating both in a rich mode where an air:fuel ratio supplied to a combustion chamber of the engine is below stoichiometric, and in a lean mode where the air:fuel ratio supplied to the combustion chamber is above stoichiometric, the method comprising:
    determining both a first parameter value of a first engine parameter and a first sensed value of an oxygen sensor disposed in an exhaust plenum of the internal combustion engine while the engine is operating at a first air:fuel ratio point in the rich mode;
    thereafter, determining both a second parameter value of the first engine parameter and a second sensed value of the oxygen sensor while the engine is operating at a second air:fuel ratio point in the rich mode, the second point being different from the first point;
    thereafter, switching operation of the engine to the lean mode and controlling operation of the engine in the lean mode based on the first sensed value, the second sensed value, the first parameter value, and the second parameter value.

2. The method of claim 1:
    wherein the determining the first sensed value comprises sensing both a resistance and a temperature associated with the oxygen sensor while the engine is operating at the first air:fuel ratio point;
    wherein the determining the second sensed value comprises sensing both a resistance and a temperature associated with the oxygen sensor while the engine is operating at the second air:fuel ratio point.

3. The method of claim 1:
    further comprising, prior to switching operation of the engine to the lean mode, determining both a third parameter value of the first engine parameter and a third sensed value of the oxygen sensor while the engine is operating at a third air:fuel point in the rich mode, the third point being different from both the first and second points;
    wherein the controlling operation of the engine in the lean mode comprises controlling operation of the engine in the lean mode further based on the third parameter value and the third sensed value.

4. The method of claim 1, wherein controlling the operation of the engine in the lean mode comprises:
    estimating a target parameter value of the first engine parameter to achieve a target air:fuel ratio based on the first sensed value, the second sensed value, the first parameter value, and the second parameter value;
    controlling the engine so that the first engine parameter assumes the target parameter value.

5. The method of claim 4:
    wherein the first parameter value is an element of a first set of parameter values corresponding to a plurality of engine parameters;
    wherein the second parameter value is an element of a second set of parameter values corresponding to the plurality of engine parameters;
    wherein the target parameter value is an element of a target set of parameter values corresponding to the plurality of engine parameters;
    wherein the controlling operation of the engine in the lean mode comprises controlling operation of the engine in the lean mode so that the plurality of engine parameter values assume their corresponding values in the target set of parameter values.

6. The method of claim 1, further comprising:
    in response to sensing at least one of a change in ambient environmental conditions and a change in engine operating conditions and a change in engine load, thereafter returning the engine to the rich mode and, while operating the engine in the rich mode:
        determining both a fifth parameter value of the first engine parameter and a fifth sensed value of the oxygen sensor while the engine is operating at a fifth air:fuel ratio point in the rich mode;
        determining both a sixth parameter value of the first engine parameter and a sixth sensed value of the oxygen sensor while the engine is operating at a sixth air:fuel ratio point in the rich mode, the sixth point being different from the fifth point;
    thereafter, returning the engine to the lean mode, and controlling operation of the engine while returned to the lean mode based on the fifth sensed value, the sixth sensed value, the fifth parameter value, the sixth parameter value, and the seventh parameter value.

7. The method of claim 1, wherein the first engine parameter is a fuel metering rate.

8. The engine control system of claim 1, wherein the oxygen sensor is a resistive-based oxygen sensor having a resistance which is uncorrelated with oxygen content when the engine is in the lean mode.

9. The engine control system of claim 1:
    further comprising determining a reference relationship between the first engine parameter and the air:fuel ratio based on the first and second sensed values, and the first and second first parameter values, as taken in the rich mode; and
    further comprising extrapolating the reference relationship into the lean mode;

wherein the controlling operation of the engine in the lean mode comprises controlling operation of the engine in the lean mode based on the extrapolated reference relationship.

10. An engine control system for an internal combustion engine, the engine capable of operating both in a rich mode where an air:fuel ratio supplied to a combustion chamber of the engine is below stoichiometric, and in a lean mode where the air:fuel ratio supplied to the combustion chamber is above stoichiometric, the engine control system comprising:
- a first oxygen sensor disposed in an exhaust plenum of the engine;
- a second engine parameter sensor configured to sense an engine parameter;
- a controller comprising one or more processing circuits, the controller operative to control operations of the engine and configured to:
  - determine both a first parameter value of a first engine parameter and a first sensed value of the oxygen sensor while the engine is operating at a first air:fuel ratio point in the rich mode;
  - thereafter, determine both a second parameter value of the first engine parameter and a second sensed value of the oxygen sensor while the engine is operating at a second air:fuel ratio point in the rich mode, the second point being different from the first point;
  - thereafter, cause the engine to switch to operating in the lean mode and control operation of the engine in the lean mode based on the first sensed value, the second sensed value, the first parameter value, and the second parameter value.

11. The engine control system of claim 10, wherein the controller is configured to control operation of the engine in the lean mode by:
- estimating a target parameter value of the first engine parameter to achieve a target air:fuel ratio based on the first sensed value, the second sensed value, the first parameter value, and the second parameter value;
- controlling the engine so that the first engine parameter assumes the target parameter value.

12. The engine control system of claim 10:
wherein the controller is configured to respond to sensing at least one of a change in ambient environmental conditions and a change in engine operating conditions and a change in engine load by temporarily returning the engine to the rich mode;
wherein the controller is configured to, while the engine is temporarily returned to the rich mode:
- determine both a fifth parameter value of the first engine parameter and a fifth sensed value of the oxygen sensor while the engine is operating at a fifth air:fuel ratio point in the rich mode;
- determine both a sixth parameter value of the first engine parameter and a sixth sensed value of the oxygen sensor while the engine is operating at a sixth air:fuel ratio point in the rich mode, the sixth point being different from the fifth point;
wherein the controller is configured to thereafter cause the engine to return to the lean mode, and control operation of the engine in the returned lean mode based on the fifth sensed value, the sixth sensed value, the fifth parameter value, and the sixth parameter value.

13. A method of controlling an internal combustion engine, the engine capable of operating both in a rich mode where an air:fuel ratio supplied to a combustion chamber of the engine is below stoichiometric, and in a lean mode where the air:fuel ratio supplied to the combustion chamber is above stoichiometric, the method comprising:
- determining both a first parameter value of a first engine parameter and a first sensed value of an oxygen sensor disposed in an exhaust plenum of the internal combustion engine while the engine is operating at a first air:fuel ratio point in the lean mode;
- thereafter, determining both a second parameter value of the first engine parameter and a second sensed value of the oxygen sensor while the engine is operating at a second air:fuel ratio point in the lean mode, the second point being different from the first point;
- thereafter, switching operation of the engine to the rich mode and controlling operation of the engine in the rich mode based on the first sensed value, the second sensed value, the first parameter value, and the second parameter value.

14. The method of claim 13:
wherein the determining the first sensed value comprises sensing both a resistance and a temperature associated with the oxygen sensor while the engine is operating at the first air:fuel ratio point;
wherein the determining the second sensed value comprises sensing both a resistance and a temperature associated with the oxygen sensor while the engine is operating at the second air:fuel ratio point.

15. The method of claim 13:
further comprising, prior to switching operation of the engine to the rich mode, determining both a third parameter value of the first engine parameter and a third sensed value of the oxygen sensor while the engine is operating at a third air:fuel point in the lean mode, the third point being different from both the first and second points;
wherein the controlling operation of the engine in the rich mode comprises controlling operation of the engine in the rich mode further based on the third parameter value and the third sensed value.

16. The method of claim 13, wherein controlling the operation of the engine in the rich mode comprises:
- estimating a target parameter value of the first engine parameter to achieve a target air:fuel ratio based on the first sensed value, the second sensed value, the first parameter value, and the second parameter value;
- controlling the engine so that the first engine parameter assumes the target parameter value.

17. The method of claim 16:
wherein the first parameter value is an element of a first set of parameter values corresponding to a plurality of engine parameters;
wherein the second parameter value is an element of a second set of parameter values corresponding to the plurality of engine parameters;
wherein the target parameter value is an element of a target set of parameter values corresponding to the plurality of engine parameters;
wherein the controlling operation of the engine in the rich mode comprises controlling operation of the engine in the rich mode so that the plurality of engine parameter values assume their corresponding values in the target set of parameter values.

18. The method of claim 13, further comprising:
in response to sensing at least one of a change in ambient environmental conditions and a change in engine operating conditions and a change in engine load, thereafter returning the engine to the lean mode and, while operating the engine in the lean mode:

determining both a fifth parameter value of the first engine parameter and a fifth sensed value of the oxygen sensor while the engine is operating at a fifth air:fuel ratio point in the lean mode;

determining both a sixth parameter value of the first engine parameter and a sixth sensed value of the oxygen sensor while the engine is operating at a sixth air:fuel ratio point in the lean mode, the sixth point being different from the fifth point;

thereafter, returning the engine to the rich mode, and controlling operation of the engine while returned to the rich mode based on the fifth sensed value, the sixth sensed value, the fifth parameter value, the sixth parameter value, and the seventh parameter value.

19. The method of claim 13, wherein the first engine parameter is a fuel metering rate.

20. The engine control system of claim 13, wherein the oxygen sensor is a resistive-based oxygen sensor having a resistance which is uncorrelated with oxygen content when the engine is in the rich mode.

21. The engine control system of claim 13:
further comprising determining a reference relationship between the first engine parameter and the air:fuel ratio based on the first and second sensed values, and the first and second first parameter values, as taken in the lean mode; and further comprising extrapolating the reference relationship into the rich mode;

wherein the controlling operation of the engine in the lean mode comprises controlling operation of the engine in the rich mode based on the extrapolated reference relationship.

22. An engine control system for an internal combustion engine, the engine capable of operating both in a rich mode where an air:fuel ratio supplied to a combustion chamber of the engine is below stoichiometric, and in a lean mode where the air:fuel ratio supplied to the combustion chamber is above stoichiometric, the engine control system comprising:

a first oxygen sensor disposed in an exhaust plenum of the engine;

a second engine parameter sensor configured to sense an engine parameter;

a controller comprising one or more processing circuits, the controller operative to control operations of the engine and configured to:

determine both a first parameter value of a first engine parameter and a first sensed value of the oxygen sensor while the engine is operating at a first air:fuel ratio point in the lean mode;

thereafter, determine both a second parameter value of the first engine parameter and a second sensed value of the oxygen sensor while the engine is operating at a second air:fuel ratio point in the lean mode, the second point being different from the first point;

thereafter, cause the engine to switch to operating in the rich mode and control operation of the engine in the rich mode based on the first sensed value, the second sensed value, the first parameter value, and the second parameter value.

23. The engine control system of claim 22, wherein the controller is configured to control operation of the engine in the rich mode by:

estimating a target parameter value of the first engine parameter to achieve a target air:fuel ratio based on the first sensed value, the second sensed value, the first parameter value, and the second parameter value;

controlling the engine so that the first engine parameter assumes the target parameter value.

24. The engine control system of claim 22:
wherein the controller is configured to respond to sensing at least one of a change in ambient environmental conditions and a change in engine operating conditions and a change in engine load by temporarily returning the engine to the lean mode;

wherein the controller is configured to, while the engine is temporarily returned to the lean mode:

determine both a fifth parameter value of the first engine parameter and a fifth sensed value of the oxygen sensor while the engine is operating at a fifth air:fuel ratio point in the lean mode;

determine both a sixth parameter value of the first engine parameter and a sixth sensed value of the oxygen sensor while the engine is operating at a sixth air:fuel ratio point in the lean mode, the sixth point being different from the fifth point;

wherein the controller is configured to thereafter cause the engine to return to the rich mode, and control operation of the engine in the returned rich mode based on the fifth sensed value, the sixth sensed value, the fifth parameter value, and the sixth parameter value.

* * * * *